(12) United States Patent
Pinchuk et al.

(10) Patent No.: US 7,431,709 B2
(45) Date of Patent: Oct. 7, 2008

(54) GLAUCOMA IMPLANT DEVICE

(75) Inventors: Leonard Pinchuk, Miami, FL (US);
Jean-Marie Parel, Miami Shores, FL (US); Francisco Fantes, Key Biscayne, FL (US); Saul Gottlieb, Miramar, FL (US); John B. Martin, Jr., Miami, FL (US); Yasushi Pedro Kato, Pembroke Pines, FL (US)

(73) Assignee: Innfocus, LLC, Miami, FL (US)

( * ) Notice: Subject to any disclaimer, the term of this patent is extended or adjusted under 35 U.S.C. 154(b) by 362 days.

(21) Appl. No.: 11/004,539

(22) Filed: Dec. 3, 2004

(65) Prior Publication Data
US 2005/0125003 A1 Jun. 9, 2005

Related U.S. Application Data

(60) Provisional application No. 60/565,291, filed on Apr. 26, 2004, provisional application No. 60/526,963, filed on Dec. 5, 2003.

(51) Int. Cl.
*A61M 5/00* (2006.01)
*A61K 9/22* (2006.01)
*A61M 31/00* (2006.01)

(52) U.S. Cl. ............... 604/8; 604/9; 604/10; 604/500; 604/890.1

(58) Field of Classification Search ............... 604/8–10, 604/289, 290, 295, 296, 500, 890.1; 606/166; 427/2.24, 2.45; 428/34.1, 34.7; 623/1, 4.1, 623/11.11; 607/1, 2, 119
See application file for complete search history.

(56) References Cited

U.S. PATENT DOCUMENTS 5,741,331 A * 4/1998 Pinchuk ............... 424/423

(Continued)

FOREIGN PATENT DOCUMENTS

WO WO02/047731 6/2002

OTHER PUBLICATIONS

A Newly Designed Glaucoma Drainage Implant Made of Poly(styrene-b-isobutylene-b-styrene), Ana C. Acosta, MD. et al., Arch Ophthalmol, vol. 124, Dec. 2006, pp. 1742-1749, available at www.archophthalmol.com.

*Primary Examiner*—Leslie Deak
*Assistant Examiner*—Phil Wiest
(74) *Attorney, Agent, or Firm*—Gordon & Jacobson, PC

(57) ABSTRACT

A surgical implant device for treating glaucoma includes an elongate duct structure formed from a material comprising polyisobutylene and a glassy segment. The material of the elongate duct structure preferably has a general block structure with a central elastomeric polyolefinic block and thermoplastic end blocks (e.g., a triblock polymer backbone comprising polystyrene-polyisobutylene-polystyrene). The elongate duct structure provides a fluid passageway for diverting aqueous humor from the anterior chamber of the eye. Preferably, the elongate duct structure defines a lumen channel having an inside diameter between 0.05 mm and 0.3 mm. The material of the elongate duct structure is biocompatible and biostable. Moreover, the material will not encapsulate in the eye and thus provides an unobstructed flowpath that diverts aqueous humor from the anterior chamber. Different embodiments of the implant device divert the aqueous humor to different parts of the eye (e.g., a space between the conjuctiva and sclera, Schlemm's canal, or a fluid reservoir formed on a posterior surface of the eye).

20 Claims, 8 Drawing Sheets

U.S. PATENT DOCUMENTS

| | | | |
|---|---|---|---|
| 5,968,058 A * | 10/1999 | Richter et al. | 606/166 |
| 6,001,128 A | 12/1999 | Graff et al. | |
| 6,102,939 A | 8/2000 | Pinchuk | |
| 6,197,240 B1 | 3/2001 | Pinchuk | |
| 6,855,770 B2 | 2/2005 | Pinchuk et al. | |
| 2003/0139729 A1 | 7/2003 | Stegmann et al. | |
| 2003/0236514 A1 * | 12/2003 | Schwarz | 604/890.1 |
| 2004/0193095 A1 | 9/2004 | Shadduck | |
| 2004/0236343 A1 | 11/2004 | Taylor et al. | |

* cited by examiner

GLAUCOMA IMPLANT DEVICE

CROSS-REFERENCE TO RELATED APPLICATIONS

The present application is a continuation-in-part of U.S. Provisional Patent Application 60/526,963, filed Dec. 5, 2003 and U.S. Provisional Patent Application 60/565,291, filed Apr. 26, 2004, both herein incorporated by reference in their entirety.

BACKGROUND OF THE INVENTION

1. Field of the Invention

This invention relates broadly to medical devices and materials for reducing intraocular pressure. More particularly, this invention relates to medical devices and materials for diverting aqueous humor out of the anterior chamber through a surgically implanted duct passageway.

2. State of the Art

Glaucoma is a disorder of the optic nerve that usually occurs in the setting of an elevated intraocular pressure (typically referred to as "IOP"). The pressure within the eye increases causing changes in the appearance ("cupping") and function ("blind spots" in the visual field) of the optic nerve. High pressure develops in an eye because of impaired outflow of aqueous. In open-angle glaucoma, the impaired outflow is caused by abnormalities of the drainage system of the anterior chamber. In closed-angle glaucoma, the impaired outflow is caused by impaired access of aqueous to the drainage system. If the pressure within the eye remains sufficiently high for a long enough period of time, total vision loss occurs. Thus, glaucoma is the number one cause of preventable blindness.

As shown in FIG. 1, the eye 10 is a hollow structure that contains a clear fluid called "aqueous humor." Aqueous humor is formed by the ciliary body 12 adjacent the posterior chamber 9 of the eye. The fluid, which is made at a fairly constant rate, then passes around the lens 14, through the pupillary opening 16 in the iris 18 and into the anterior chamber 20. Once in the anterior chamber 20, the fluid drains out of the eye 10 through two different routes. In the "uveoscleral" route, the fluid percolates between muscle fibers of the ciliary body 12. This route accounts for approximately ten percent of the aqueous outflow in humans. The primary pathway for aqueous outflow in humans is through the "canalicular" route that involves the trabecular meshwork 22 and Schlemm's canal 24.

The trabecular meshwork 22 and Schlemm's canal 24 are located at the junction between the iris 18 and the sclera 26, which is typically referred to as the "angle". The trabecular meshwork 22 is a wedge-shaped structure that runs around the circumference of the eye. It is composed of collagen beams arranged in a three-dimensional sieve-like structure. The beams are lined with a monolayer of cells called trabecular cells. The spaces between the collagen beams are filled with an extracellular substance that is produced by the trabecular cells. These cells also produce enzymes that degrade the extracellular material. Schlemm's canal 24 is disposed adjacent to the trabecular meshwork 22. The outer wall of the trabecular meshwork 22 coincides with the inner wall of Schlemm's canal 24. Schlemm's canal 24 is a tube-like structure that runs around the circumference of the cornea. In human adults, Schlemm's Canal is believed to be divided by septa into a series of autonomous, dead-end canals.

The aqueous fluid travels through the spaces between the trabecular beams of the trabecular meshwork 22, across the inner wall of Schlemm's canal 24 into the canal, through a series of about twenty-five collecting channels that drain from Schlemm's canal 24 and into the episcleral venous system 28.

In a normal patient, aqueous production is equal to aqueous outflow and intraocular pressure remains fairly constant (typically in the 15 to 21 mmHg range). In glaucoma, there is abnormal resistance to aqueous outflow, which manifests itself as increased IOP. Tonometry is the measurement of IOP.

In primary open angle glaucoma, which is the most common form of glaucoma, the abnormal resistance is believed to be along the outer aspect of trabecular meshwork 22 and the inner wall of Schlemm's canal 24. Primary open angle glaucoma accounts for approximately eighty-five percent of all glaucoma. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid builds up, the IOP within the eye increases. The increased IOP compresses the axons in the optic nerve and also may compromise the vascular supply to the optic nerve. The optic nerve carries vision from the eye to the brain. Some optic nerves seem more susceptible to IOP than other eyes. While research is investigating ways to protect the nerve from an elevated pressure, the therapeutic approach currently available in glaucoma is to reduce the intraocular pressure.

The clinical treatment of glaucoma is typically carried out in a step-wise manner. Medication often is the first treatment option. Administered either topically or orally, these medications work to either reduce aqueous production or they act to increase outflow. Currently available medications have many serious side effects including: congestive heart failure, respiratory distress, hypertension, depression, renal stones, aplastic anemia, sexual dysfunction and death. Compliance with medication is a major problem, with estimates that over half of glaucoma patients do not follow their correct dosing schedules.

When medication fails to adequately reduce the pressure, laser trabeculoplasty often is performed. In laser trabeculoplasty, thermal energy from a laser is applied to a number of noncontiguous spots in the trabecular meshwork. It is believed that the laser energy stimulates the metabolism of the trabecular cells in some way, and changes the cellular material in the trabecular meshwork. In a large percent of patients, aqueous outflow is enhanced and IOP decreases. However, the effect often is not long lasting and a significant percentage of patients develop an elevated pressure within the years that follow the treatment. The laser trabeculoplasty treatment is typically not repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not reduce the pressure sufficiently, then incisional surgery (typically referred to as filtering surgery) is performed. With incisional surgery, a hole is made in the sclera 26 adjacent the angle region. This hole allows the aqueous fluid to leave the eye through an alternate route.

The most commonly performed incisional procedure is a trabeculectomy. In a trabeculectomy, a posterior incision is made in the conjunctiva 30, which is the transparent tissue that covers the sclera 26. The conjunctiva 30 is rolled forward, exposing the sclera 26 at the limbus 32, which marks the junction between the sclera 26 and the cornea 34. A partial scleral flap is made and dissected into the cornea. The anterior chamber 20 is entered beneath the scleral flap, and a section of deep sclera 26 and trabecular meshwork 20 is excised. The scleral flap is loosely sewn back into place. The conjunctiva incision is tightly closed. Post-operatively, the aqueous fluid passes through the hole, beneath the scleral flap and collects in a bleb formed beneath the conjunctiva 30. The fluid then is either absorbed through blood vessels in the conjunctiva 30 or traverses across the conjunctiva 30 into the tear film. Trabeculectomy surgery of this nature is extremely difficult and only a small fraction of ophthalmologists perform this procedure. In addition, it is very time consuming and physicians are not reimbursed for the time it takes to perform the surgery and it is therefore rarely performed.

When trabeculectomy doesn't successfully lower the eye pressure, the next step, and usually the last, is a surgical procedure that implants a device that shunts aqueous humor to control the IOP. One such implant device, as shown in U.S. Pat. No. 6,050,970 to Baerveldt, is a drainage tube that is attached at one end to a plastic plate. The drainage tube is a flow tube between 1.0 and 3.0 French (and preferably with an inner diameter of 0.3 mm and an outer diameter of 0.6 mm). An incision is made in the conjunctiva 30, exposing the sclera 26. The plastic plate is sewn to the surface of the eye posteriorly, usually over the equator. A full thickness hole is made into the eye at the limbus 32, usually with a needle. The tube is inserted into the eye through this hole. The external portion of the tube is covered with either sclera or other tissue. The conjunctiva 30 is replaced and the incision is closed tightly. With this shunt device, aqueous drains out of the eye through the silicone tube to the bleb, which is a thin layer of connective tissue that encapsulates the plate and tube and then to the surface of the eye. Aqueous drains out of the bleb and to the surface of the eye. Deeper orbital tissues then absorb the fluid. The plate typically has a large surface area in order to wick and disperse fluid, which facilitates absorption of fluid in the surrounding tissue. These disks are generally made of silicone rubber, which serves to inhibit tissue adhesion as the plate becomes encapsulated by the connective tissue of the bleb. The disks can be as large as 10 mm in diameter and are irritating to some patients.

Other implant devices are shown in U.S. Pat. No. 6,468,283 to Richter et al. and U.S. Pat. No. 6,626,858 to Lynch et al., respectively. The Richter implant device is a tubular structure that shunts aqueous humor from the anterior chamber to a space between the conjunctiva 30 and the sclera 26. The Lynch implant device is a tubular structure that shunts aqueous humor from the anterior chamber through the trabecular meshwork 22 and into Schlemm's canal 24. These implant devices are described as being formed from silicone, Teflon, polypropylene, stainless steel, etc. These implant devices also typically require precise placement away from the angle and the iris in order to prevent interference with the iris and/or to avoid occlusion of the drainage lumen by ocular tissue (for example, the fibrous tissue of the iris and/or the sclera that may plug the drainage lumen). In addition, such implant devices typically include a unidirectional valve to minimize hypotony (low IOP) in the anterior chamber of the eye. However, the desired flow control provided by such valves is difficult to maintain and are prone to failure. Lastly, these shunt devices are relatively stiff and have been shown to erode through the ocular tissue wall adjacent thereto over time.

Thus, there remains a need in the art to provide an implant device for the treatment of glaucoma that is realized from a biocompatible material which will not encapsulate in the eye and that enables control over IOP without the need for large surface area plates and possibly without the need for unidirectional flow control valves.

SUMMARY OF THE INVENTION

It is therefore an object of the invention to provide an implant device for the treatment of glaucoma that is realized from a biocompatible material that will not encapsulate in the eye, thereby avoiding occlusion of the implant device by ocular tissue.

It is another object of the invention to provide an implant device for the treatment of glaucoma that is realized from a biocompatible material that will not encapsulate in the eye, thereby enabling control over IOP without the need for a large diameter plate.

It is a further object of the invention to provide an implant device for the treatment of glaucoma that utilizes a small size duct structure, thereby enabling more flexible and less precise positioning of the duct structure within the ocular cavity and also enabling multiple devices to be implanted, if necessary.

In accord with these objects, which will be discussed in detail below, a surgical implant device for treating glaucoma includes an elongate duct structure formed from a polymeric material comprising polyisobutylene and a glassy segment. The elongate duct structure provides a fluid passageway for diverting aqueous humor from the anterior chamber of the eye. Preferably, the elongate duct structure defines a lumen channel having a diameter greater than 0.05 mm and less than 0.5 mm, most preferably in the range between 0.1 mm and 0.3 mm. The polymeric material of the duct structure is biocompatible and biostable. Moreover, the polymeric material will not encapsulate in the eye and thus an elongate duct formed from SIBS material provides an unobstructed flowpath that diverts aqueous humor from the anterior chamber without the need for a large diameter plate commonly used in the prior art designs.

According to one embodiment of the invention, the surgical implant device diverts the aqueous humor to Schlemm's canal.

According to another embodiment of the invention, the surgical implant device diverts the aqueous humor to a fluid reservoir formed in a space between the conjuctiva and sclera.

According to yet another embodiment of the invention, the surgical implant device diverts the aqueous humor to a fluid reservoir formed on a posterior surface of the eye.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
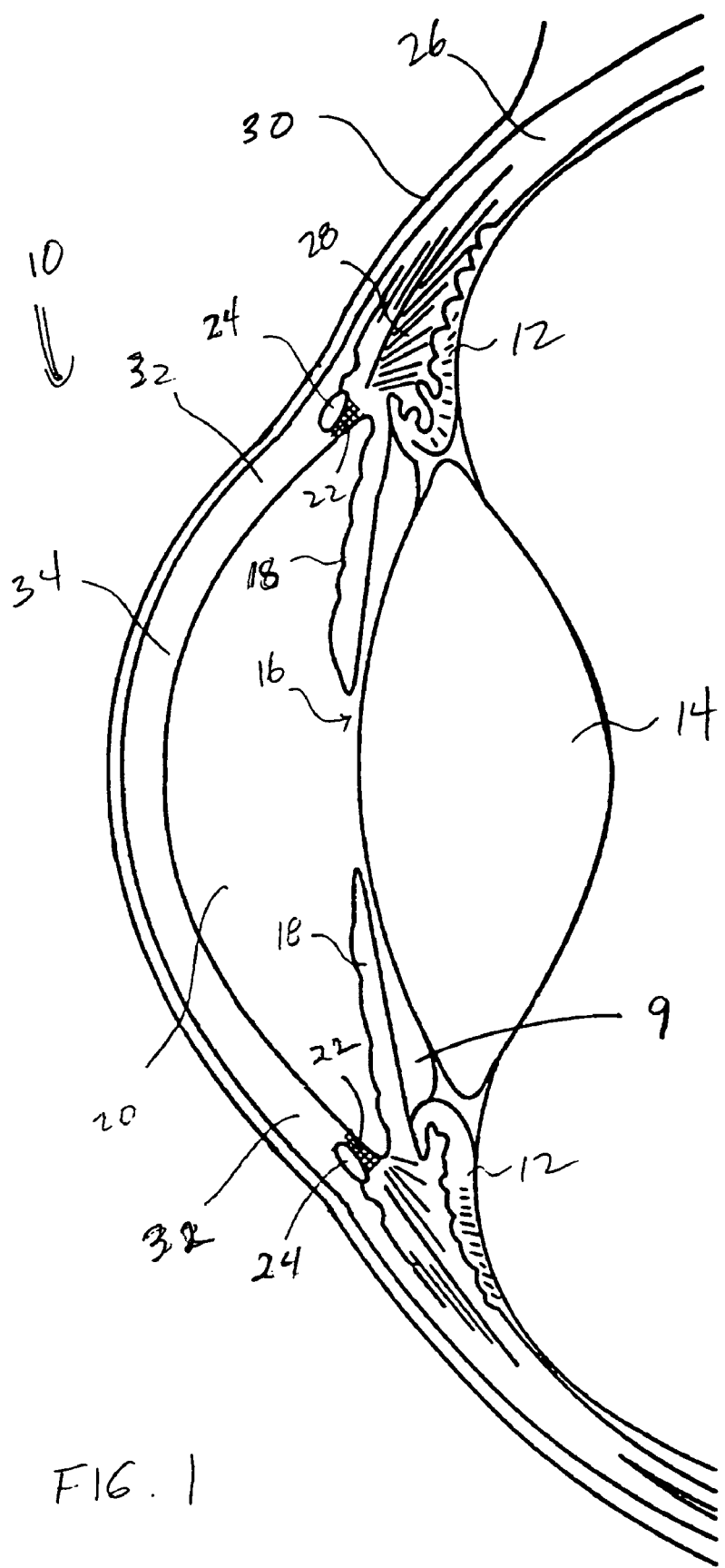
FIG. 1 is a prior art illustration showing anatomic details of the human eye.
Figure 2:
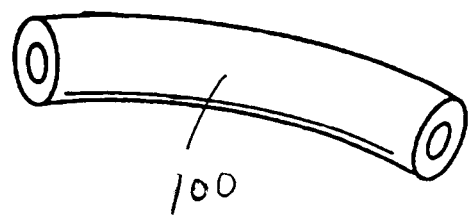
FIG. 2 is an illustration showing a side view of an aqueous drainage tube realized by SIBS material in accordance with the present invention.

Turning now to FIG. 2, there is shown an aqueous drainage tube 100 for treating glaucoma in accordance with the present invention. The aqueous drainage tube is formed from a polyolefinic copolymer material having a triblock polymer backbone comprising polystyrene-polyisobutylene-polystyrene, which is herein referred to as "SIBS". High molecular weight polyisobutylene (PIB) is a soft elastomeric material with a Shore hardness of approximately 10A to 30A. When copolymerized with polystyrene, it can be made at hardnesses ranging up to the hardness of polystyrene, which has a Shore hardness of 100D. Thus, depending on the relative amounts of styrene and isobutylene, the SIBS material can have a range of hardnesses from as soft as Shore 10A to as hard as Shore 100D. In this manner, the SIBS material can be adapted to have the desired elastomeric and hardness qualities. Details of the SIBS material is set forth in U.S. Pat. Nos. 5,741,331; 6,102,939; 6,197,240; 6,545,097, which are hereby incorporated by reference in their entirety.

The SIBS material of the aqueous drainage tube 100 may be polymerized under control means using carbocationic polymerization techniques such as those described in U.S. Pat. Nos. 4,276,394; 4,316,973; 4,342,849; 4,910,321; 4,929,683; 4,946,899; 5,066,730; 5,122,572; and Re 34,640, each herein incorporated by reference in its entirety. The amount of styrene in the copolymer material is preferably between about 5 mole % to 30 mole %. The styrene and isobutylene copolymer materials are preferably copolymerized in solvents.

The aqueous drainage tube 100 is preferably formed by extrusion of SIBS material over a thin wire having a diameter between 40 μm and 100 μm, and most preferably 60 μm. The inside diameter of the aqueous drainage tube 100 is preferably in the range between 0.05 mm and 0.2 mm, while the outside diameter of the aqueous drainage tube 100 is preferably in the range between 0.2 mm and 0.9 mm. Inside diameter dimensions in the range between 0.1 mm and 0.3 mm are most preferred because such dimensions limit aqueous flow through the tube and thus provide for control over IOP without the need for unidirectional valves. The length of the tube 100 is preferably between 20 mm and 30 mm, and most preferably 24 mm.

Advantageously, the SIBS material of the aqueous drainage tube 100 provides superb biocompatibility and biostability characteristics. Moreover, animal tests have shown that surprisingly it will not encapsulate in the eye, and thus can be used to provide unobstructed drainage from the anterior chamber of the eye.

It is expected that alternative polymeric materials are suitable for the practice of the present invention. Such alternative polymeric materials preferably include polyisobutylene-based material capped with a glassy segment. The glassy segment provides a hardener component for the elastomeric polyisobutylene. The glassy segment preferably does not contain any cleavable group which will release in the presence of body fluid inside the human eye and cause toxic side effects and cell encapsulation. The glassy segment can be a vinyl aromatic polymer (such as styrene, α-methylstyrene, or a mixture thereof), or a methacrylate polymer (such as methylmethacrylate, ethylmethacrylate, hydroxymethalcrylate, or a mixture thereof). Such materials preferably have a general block structure with a central elastomeric polyolefinic block and thermoplastic end blocks. Even more preferably, such materials have a general structure:

BAB or ABA (linear triblock), $B(AB)_n$, or $a(BA)_n$ (linear alternating block), or $X-(AB)_n$, or $X-(BA)_n$ (includes diblock, triblock and other radial block copolymers), where A is an elastomeric polyolefinic block, B is a thermoplastic block, n is a positive whole number and X is a starting seed molecule.

Such materials may be star-shaped block copolymers (where n=3 or more) or multi-dendrite-shaped block copolymers. These materials collectively belong to the polymeric material referred to herein as SIBS material.

Figure 3:
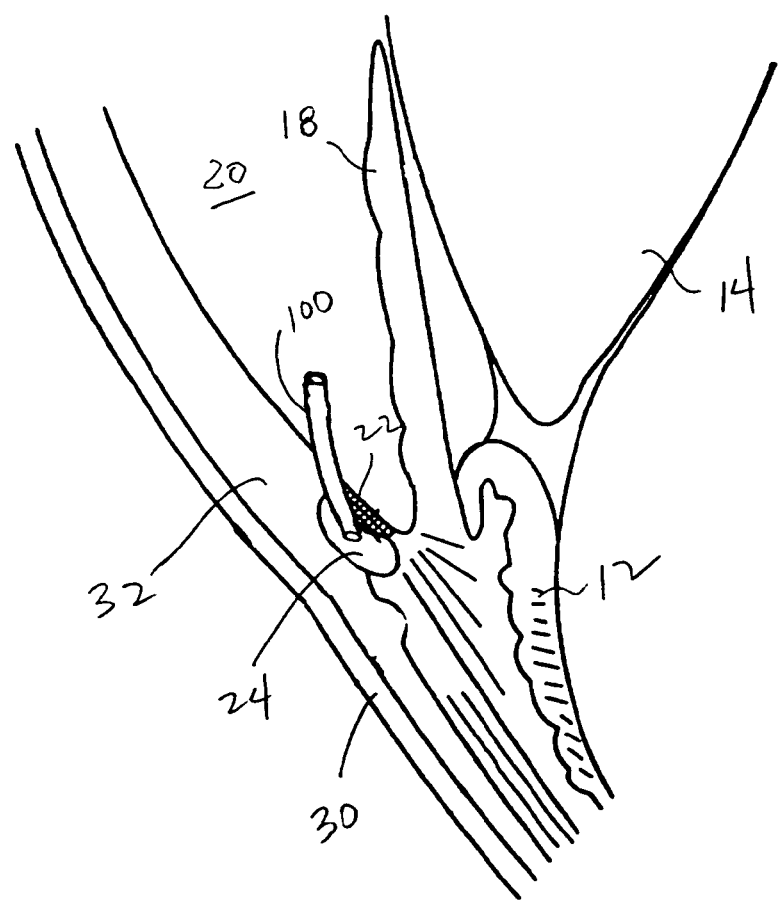
FIG. 3 is an illustration showing the aqueous drainage tube of FIG. 2 placed within Schlemm's canal to provide a flow path for aqueous humor from the anterior chamber of the eye through the trabecular meshwork and into Schlemm's canal.

Turning now to FIG. 3, there is shown the aqueous drainage tube 100 of FIG. 2 placed within Schlemm's canal 24 to provide a flow path for aqueous humor from the anterior chamber 20 through the trabecular meshwork 22 and into Schlemm's canal 24. The length of the tube 100 can be in the range from 1.0 mm to 40 mm and preferably about 6.0 mm. The inside diameter of the tubular structure is preferably about 0.1 mm. The tube 100 is preferably implanted through a conjunctival flap. A partial thickness scleral flap is then created and the exterior aspect of Schlemm's canal 24 is identified and entered. The drainage tube 100 is then inserted through the inner wall of Schlemm's canal 24 and the trabecular meshwork 22 into the anterior chamber 20 of the eye. In some cases, an incision may be needed through the inner wall of Schlemm's canal 24 and through the trabecular meshwork 22 into the anterior chamber 20 in order to facilitate insertion of the drainage tube 100. The scleral flap and the conjuctival wound are then closed in a conventional manner. In this configuration, the drainage tube 100 provides a flow path for aqueous humor from the anterior chamber 20 through the trabecular meshwork 22 and into Schlemm's canal 24. Advantageously, the SIBS material of the aqueous drainage tune 100 provides superb biocompatibility and biostability characteristics. Moreover, the fibrous tissue of the eye, including the tissue of the Schlemm's canal 24 and the trabecular meshwork 22 will not encapsulate the SIBS material of the drainage tube 100, thus minimizing the risk of obstruction of the tube. In addition, the dimensions of the drainage tube 100 can be made small such that aqueous flow through the tube 100 is limited and thus provide for control over IOP without the need for a unidirectional valve.

Figure 4:
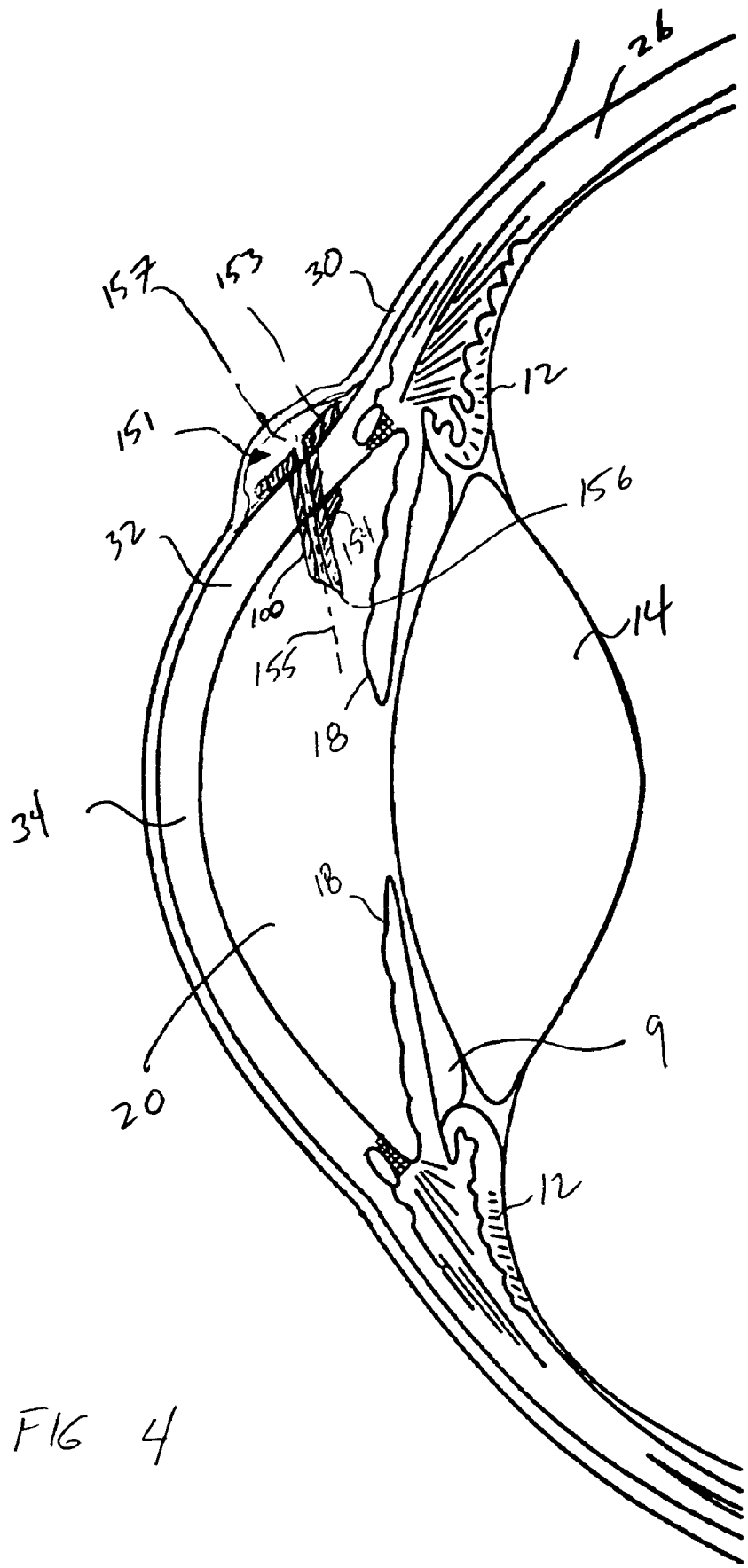
FIG. 4 is an illustration showing an aqueous drainage device that employs the drainage tube structure of FIG. 2 to shunt aqueous humor from the anterior chamber to a space between the conjunctiva and the sclera of the eye.

Turning now to FIG. 4, there is shown an aqueous drainage device 151 that employs the drainage tube 100 of FIG. 2 to shunt aqueous humor from the anterior chamber 20 to a space between the conjunctiva 30 and the sclera 26. The device 151 includes a disk 153 and a retention member 154 that are each disposed at respective angles with respect to the tube 100 which correspond to the angle between the sclera and the desired axis of insertion 155 as shown. The disk 153 and the retention member 154 are spaced apart at a distance corresponding to the thickness of the sclera at the desired implant location. The axis 155 lies along the central axis of the tube 100. A needle like tip 156 is formed at the inlet end of the tube 100. The device 151 can be very small; for example, the tube 100 may have a length of about 2 mm and an inside diameter of 0.1 mm, and the disk 153 may have a diameter of 0.5 mm. The device 151 is preferably implanted through a conjunctival flap. The implant location in the sclera 26 is located and the device 151 is pushed through the sclera 26 at the implant location. The acute angle of the tip 156 ensures that the device 151 enters the sclera 26 easily. The disk 153 and the retention member 154 cooperate to anchor the device 151 at it is proper position. In some cases, an incision may be needed through (or partially through) the outer wall of the sclera 26 in order to facilitate insertion of the drainage tube 100. The conjuctival wound is then closed in a conventional manner. Postoperatively and during operation of the device 151, a fluid reservoir 57 forms in the space between the conjunctiva 30 and the sclera 26 over the disk 153 as shown. In this configuration, the drainage tube 100 of the device 151 provides a flow path for aqueous humor from the anterior chamber 20 and into the fluid reservoir 157, which provides resistance to aqueous outflow therefrom.

Note that the location of the device 151 in the eye is not limited to that shown and thus may be any other suitable position. Moreover, the entire device 151 may be formed from a SIBS material by a suitable molding operation. Advantageously, the SIBS material of the device 151 provides superb biocompatibility and biostability characteristics. Moreover, the SIBS material of the device 151 resists encapsulation by the fibrous tissue of the eye, including the tissue of the sclera 26 and the iris 18, thus minimizing the risk of obstruction of the aqueous drainage device. In addition, the dimensions of the drainage tube 100 of the device can be made small such that aqueous flow through the tube 100 is limited and thus provide for control over IOP without the need for a unidirectional valve.

Figure 5:
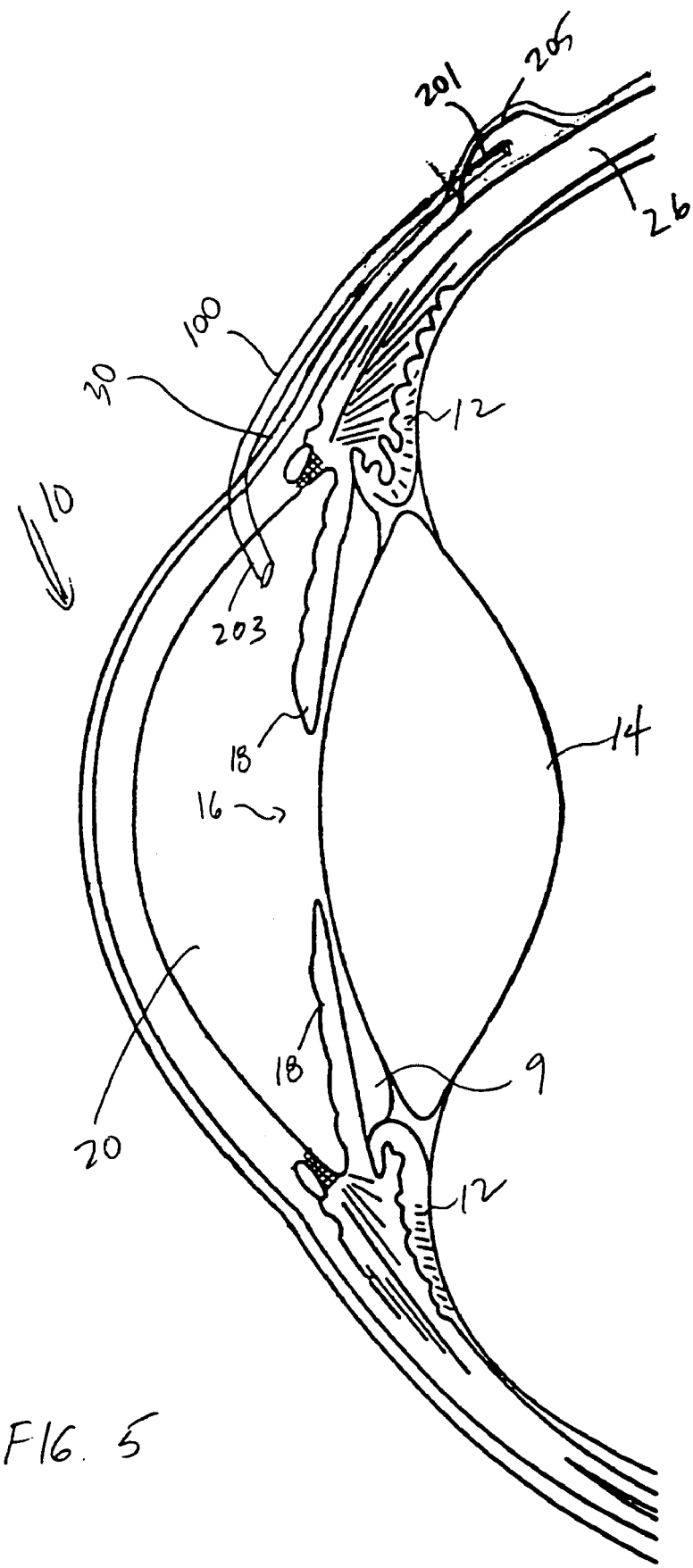
FIG. 5 is an illustration showing the aqueous drainage tube of FIG. 2 wherein with one end positioned in a posterior surface of the eye and the other end passing through the sclera and into the anterior chamber of the eye.

Turning now to FIG. 5, there is shown the aqueous drainage tube of FIG. 2 with one end positioned in a posterior surface of the eye and the other end passing through the sclera 26 and into the anterior chamber 20 of the eye. More particularly, the eye includes six ocular eye muscles which control the movement of the eye in its socket. The eye muscles include the rectus muscles (which comprise the lateral, medial, superior, and inferior) and the oblique muscles (which comprise the superior and inferior). The muscle insertion point is the point in which the rectus muscles attach to the globe of the eye. The globe of the eye is logically partitioned into two parts: an anterior portion (also referred to as the anterior segment) and a posterior portion (also referred to as the posterior segment). The anterior portion is anterior to the muscle insertion point, while the posterior portion is posterior to the muscle insertion point. One end 201 of the tubular structure 100 is positioned within the posterior portion of the globe of the eye, while the other end 203 of the tube 100 is inserted through the conjunctiva 30 and sclera 26 into the anterior chamber 22 of the eye as shown. A connective tissue graft (not shown), or possibly a graft formed from a biocompatible material, may be used to cover and support the drainage tube 100 close to the outer surface (e.g., conjunctiva 30 and/or Tenon's capsule) of the globe of the eye. During the implantation of the aqueous drainage tube and postoperatively, a fluid capsule 205 forms in the space between the outer sheath (e.g., the conjunctiva 30 or Tenon's capsule) and the sclera 26 in the vicinity of the tube end 201 as shown. In this configuration, the drainage tube 100 provides a flow path for aqueous humor from the anterior chamber 20 and into the fluid capsule 205, which provides resistance to aqueous outflow therefrom. Note that the location of the tubular structure 100 in the eye is not limited to that shown and thus may be any other suitable position. In addition, multiple fenestrations can be added to the side of a section of the drainage tube 100 to facilitate drainage along the tube section. The drainage tube 100 preferably has a length of 10 mm to 15 mm and an inside diameter between 0.1 mm and 0.3 mm. Advantageously, the SIBS material of the tube 100 provides superb biocompatibility and biostability characteristics. Moreover, the SIBS material of the tube 100 resists encapsulation by the fibrous tissue of the eye, including the tissue of the conjunctiva, Tenon's capsule, sclera 26 and the iris 18, thus minimizing the risk of obstruction of the aqueous drainage device. Such resistance to encapsulation also provides for suitable aqueous drainage without the need for a large posterior plate, which is irritating and unsightly to some patients. In addition, the dimensions of the drainage tube 100 can be made small such that aqueous flow through the tube 100 is limited and thus provide for control over IOP without the need for a unidirectional valve.

Figure 6:
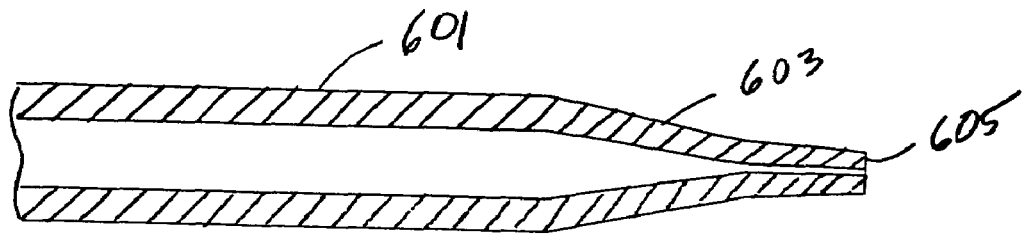
FIG. 6 is an illustration of a SIBS-based aqueous drainage tube with a duck-bill-type flow control valve formed on its end in accordance with the present invention.
Figure 7:
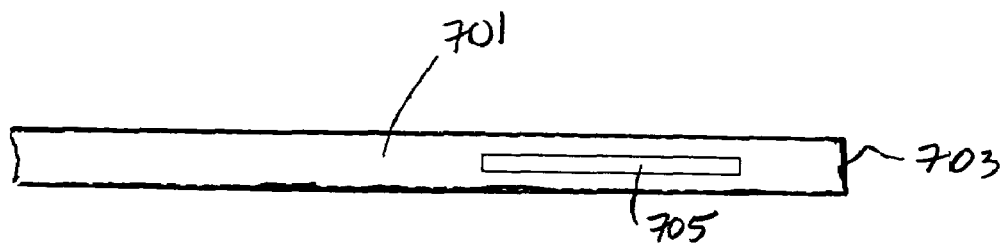
FIG. 7 is an illustration of a SIBS-based aqueous drainage tube with a slit-type flow control valve formed on its side in accordance with the present invention.

The aqueous drainage devices described herein can readily be adapted to incorporate a duck-billed-type flow control valve as shown in FIG. 6, or a slit-type flow control valve as shown in FIG. 7.

The duck-billed-type flow control valve of FIG. 6 includes a tube 601 realized from SIBS material having a thermo-formed tapered end 603 whose cross-sectional inside and outside diameter at its tip 605 is smaller than that of the tube 601. Aqueous can flow unidirectionally through the tube from left to right but not backwards. The fluid pressure required to open the valve (e.g., and allow bidirectional fluid flow) can be adjusted by varying the length of the tapered end 603 as well as the stiffness of the material.

The slit-type flow control valve of FIG. 7 includes a tube 701 realized from SIBS material having a closed end 703. One or more slits (one shown as 705) are cut through the tube along its length to allow fluid to aqueous to leak out. Aqueous can flow unidirectionally from inside the tube 701 through the slit 705 but not backwards. The fluid pressure required to open the valve (e.g., and allow bidirectional fluid flow) can be adjusted by varying the wall thickness as well as the length of the slit and elasticity of the SIBS material of the tube 701. The slit valve(s) can be located at the proximal end or distal ends of the tube 701, or throughout the tube 701.

Figure 8:
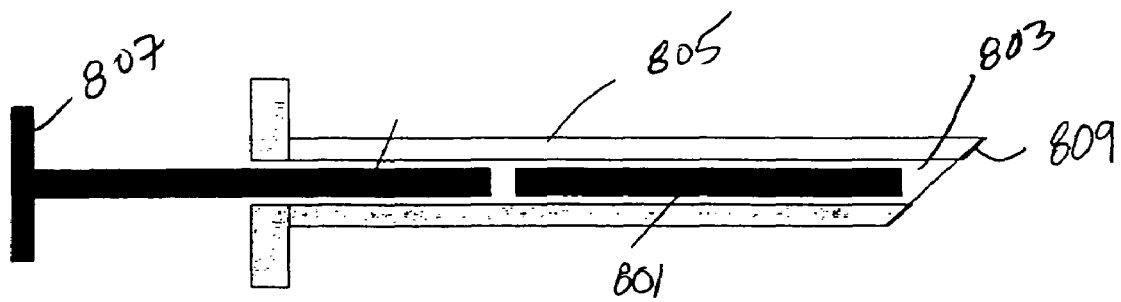
FIG. 8 is a schematic illustration of a deployment mechanism for the aqueous drainage tube of FIG. 2 in accordance with the present invention.

FIG. 8 illustrates a first embodiment of a delivery device for inserting the tubular aqueous drainage devices described herein into the anterior chamber of the eye. The tubular aqueous drainage device 801 is loaded into the lumen 803 of a needle 805, which for example can be between 22 and 30 gauge. A plunger 807 is inserted into the lumen 803 proximal to the device 801. The tip 809 of the needle 805 is inserted into the anterior chamber of the eye. While the plunger 807 is held steady, the needle 805 is withdrawn thereby leaving the device 801 in place with its distal end inside the anterior chamber of the eye. The proximal end of the device 801 can be placed between the sclera and conjunctiva of the eye (similar to the embodiment shown in FIG. 4).

Figure 9A:
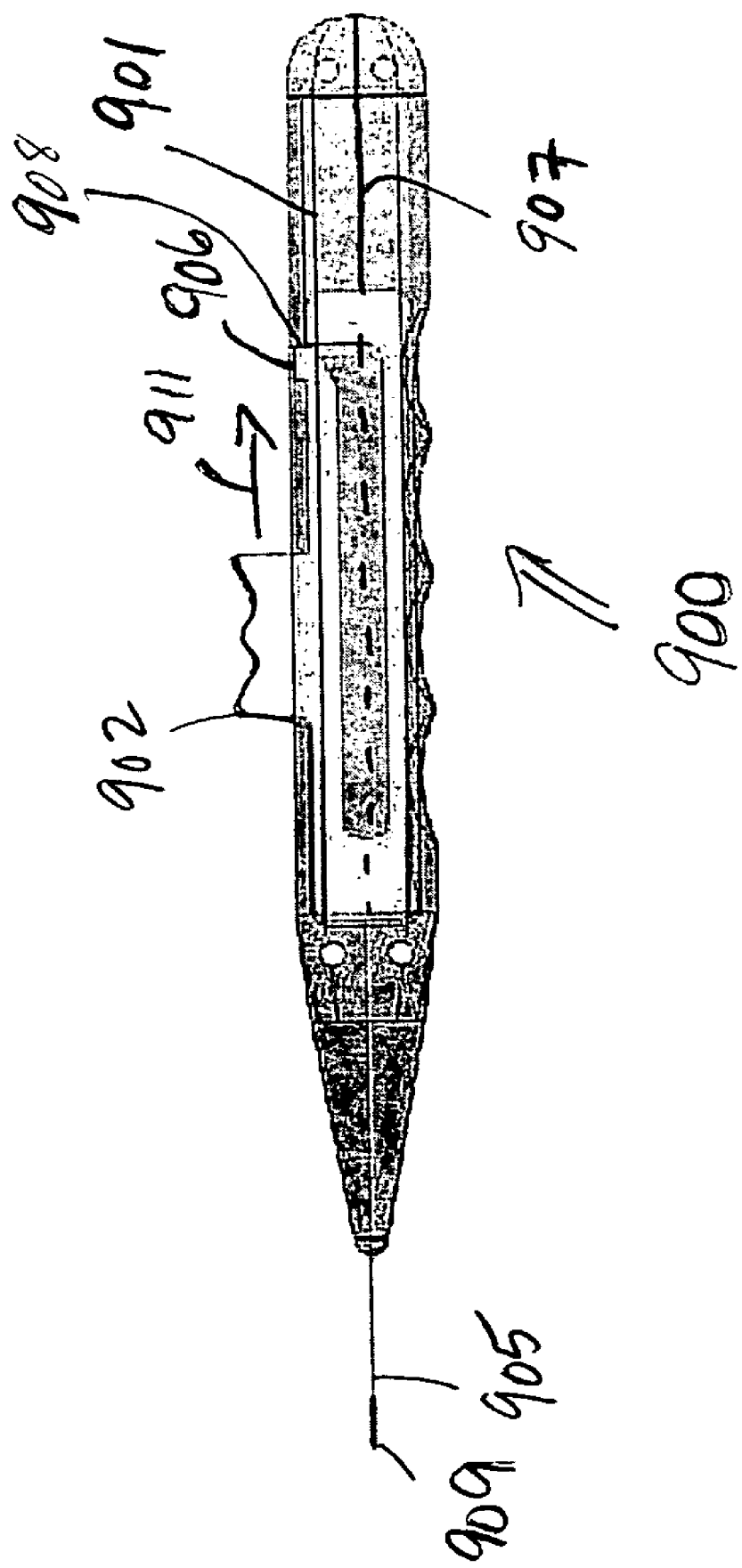
FIGS. 9A and 9B are schematic illustrations of an alternate deployment mechanism for the aqueous drainage tube of FIG. 2 in accordance with the present invention.
Figure 9B:
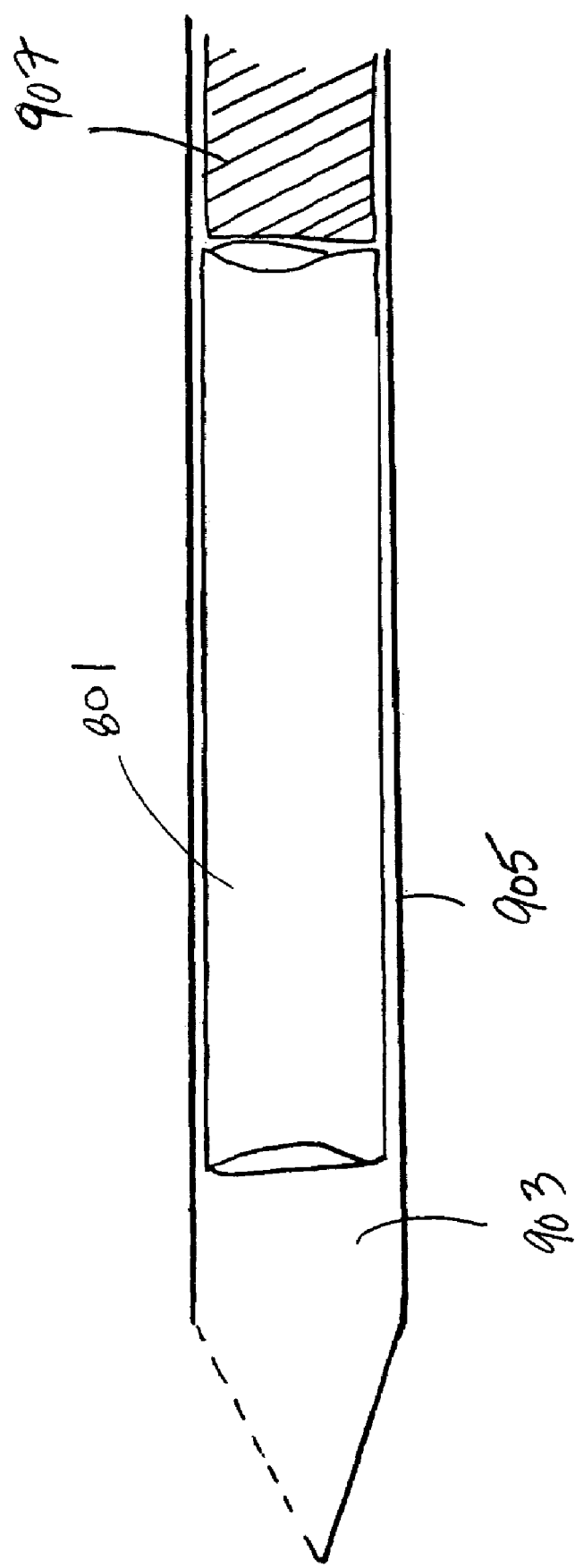

FIGS. 9A and 9B illustrate a second embodiment of a delivery device for inserting the tubular aqueous drainage devices described herein into the anterior chamber of the eye. The delivery device 900 includes a handle body 901 with a manually-actuated retraction lever 902. The retraction lever 902 is mated to a retractable needle 905, which for example can be between 22 and 30 gauge. The tubular aqueous drainage device 801 is loaded into the lumen 903 of the retractable needle 905 (FIG. 9B). A stationary wire 907 extends from the rear section of the handle body 901 and through a passageway in the retraction lever 902 into the lumen 903, where it butts up against the proximal end of the drainage device 801 (FIG. 9B). The retraction lever 902 includes a locking nub 906 that normally butts up against a wall 908 of the handle body. Downward finger pressure is applied the retraction lever 902, which moves the locking nub 906 downward such that the lever 902 can be retracted rearward in the direction of arrow 911 by finger pressure. In use, the tip 909 of the needle 905 is inserted into the anterior chamber of the eye. While the handle body 901 is held steady, the lever 902 is pressed downward to release the locking nub 906 and then manually retracted (in the direction of the arrow 911), which causes the needle 905 to be withdrawn thereby leaving the device 801 in place with its distal end inside the anterior chamber of the eye. The proximal end of the device 801 can be placed between the sclera and conjunctiva of the eye (similar to the embodiment shown in FIG. 4). It will be apparent to one skilled in the art that alternative ways to retract the needle may be employed by the delivery device 900. Advantageously, the delivery device 900 can be operated with one hand to insert and deliver the aqueous humor drainage device into the anterior chamber of the eye.

Figure 10A:
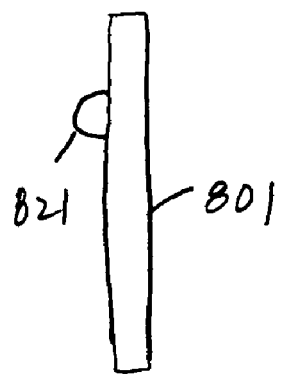
FIGS. 10A, 10B and 10C illustrate various mechanisms for fixing the aqueous drainage tube of FIG. 2 to the eye in accordance with the present invention.
Figure 10B:
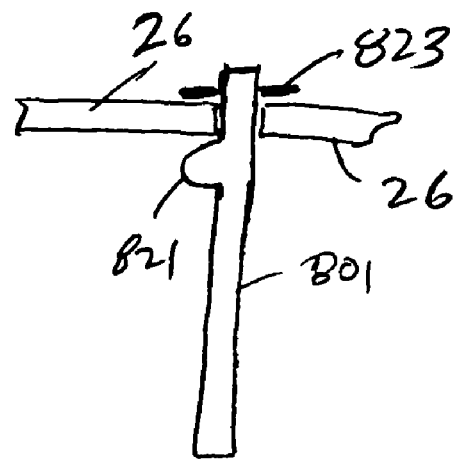

It is contemplated that fixation of the device 801 to the eye may be aided by one or more various means. For example, one or more suture threads may be wrapped around the tubular device 801. The suture thread(s) are positioned in the scleral opening and may elicit enough scarring and tissue encapsulation in the area adjacent the scleral opening in order to affix the device 801 in place. The suture thread(s) may also be tied to the sclera 26 of the eye to affix the device 801 in place. Alternatively, the suture threads may be attached to a tab (or other structure) which projects from the tubular device at or near its proximal end and then tied to the sclera 26. In another example, a silicon sleeve (or other material such as collagen, a porous SIBS-based tube section) may be disposed about the tubular device 801 at the scleral opening. This material promotes scarring at the scleral opening that affixes the device 801 in place. In yet another example, a suitable glue (such as silastic adhesive) may be applied to the tubular device 801 such that it chemically binds to the scleral opening in order to affix the device 801 in place. In yet another example, mechanical features may be added to the tubular device 801 to limit posterior and/or anterior movement of the device. As shown in FIG. 10A, such mechanical features may include a tab 821. The tab 821 rides along a longitudinal slit (not shown) in the delivery needle during delivery into the anterior chamber of the eye. After such delivery, the top surface of the tab 821 butts up against the sclera 26 around the scleral opening (FIG. 10B) to prevent posterior movement of the device 801.

Figure 10C:
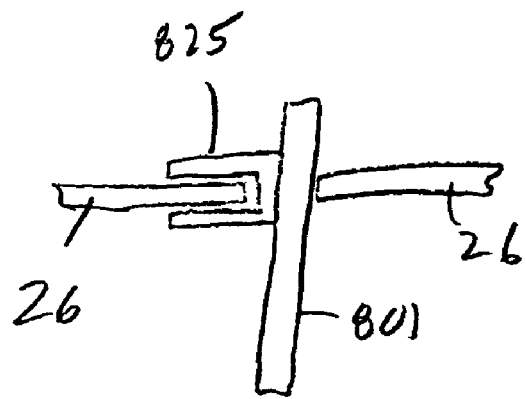

In lieu of the tab 821, or in addition thereto, an o-ring 823 (or other suitable fastener) may be provided that is disposed about the outer surface of the delivery needle and pushed onto the outer surface of the device 801 outside the eye. It is positioned adjacent the sclera 26 to prevent anterior movement of the device 801. Similarly, the tissue gripping functionality of the combination of the tab 821 and the o-ring 823 can be obtained through use of a flexible clip 825 attached to the side of the tubular device 801 as shown in FIG. 10C.

In another aspect of the present invention, the inner wall of the lumen of the SIBS-based tubular aqueous drainage devices described herein may be treated with an agent (such as hyaluronic acid, phosphatidyl choline, or glycerin (glycerol)) that prevents the lumen from sticking closed in the event that it is pinched, for example, with forceps or the like.

In an exemplary manufacturing process, a SIBS material having a triblock polymer backbone comprising polystyrene-polyisobutylene-polystyrene is extruded over a thin wire (e.g., 0.0025" in diameter), and placed in a solution of isopropyl alcohol and glycerin (preferably 95% isopropyl alcohol and 5% glycerin by weight) for a period of time between 5 and 24 hours at 60° C. which causes the SIBS-based tubular structure formed over the wire to swell. The swelled tubular structure is rinsed in isopropyl alcohol and then removed from the wire. After removal, the SIBS-based tubular structure is placed in an oven preferably at a temperature of 80° C. for 30-60 minutes to flash off residual isopropyl alcohol. The temperature of the oven is then increased to 110° C. for 30 minutes for sterilization. The SIBS-based tubular structure is then removed from the oven and allowed to cool. The resulting tubular structure will contain some glycerin which will reduce sticking. The SIBS-based tubular structure may be packaged in a PTFE heat shrink tube and sealed in a pouch, which is preferably realized from a polyester film such as Mylar®, for storage and distribution.

The biocompatibility and biostablity of the SIBS material for the aqueous drainage devices described herein is supported by the following non-limiting example.

Materials and Methods: SIBS material having a triblock polymer backbone comprising polystyrene-polyisobutylene-polystyrene with mole percent styrene content 9.8%, 21.5% and 23.4%, respectively, were synthesized by living end carbocationic polymerization techniques. Also synthesized was a control material made from medical grade polydimethylsiloxane (PDMS, RI=1.41). Both the SIBS material and the PDMS material were compression molded at 160° C. into flat disks, 3 mm and 6 mm diameter, all being 300 μm thick. The disks were implanted in four groups of two New Zealand White rabbits using conventional surgical techniques. Maxitrol topical ointment was given for three days. No medications were given thereafter. Full ophthalmic examinations were performed weekly using a slit-lamp biomicroscope. Two animals with an endocapsular implant (intraocular lens) were followed until the eighth week and six animals with intracorneal and subtenon implants were followed until the twelfth week before euthanasia for histology.

Results: No inflammation, infection, toxic reaction and implant migration were observed. The cornea, sclera, iris, ciliary body, choroids, vitreous and retina remained normal in all animals. No neovasculaization or fibrosis could be detected around any SIBS disks implanted intracorneally. Subtenon PDMS control implants elicited a moderate neovascularization reaction whereas the SIBS samples did not. Encapsulation was approximately 200 μm for PDMS and was well organized and consistent around the sample. In addition, gross histology showed neovascularization (an ingrowth of capillaries) radiating from the sample. The histology for the SIBS samples routinely demonstrated a loose unorganized fibrous network with variable thickness ranging from 0 to 100 μm around the sample with no signs of neovascularization. Scanning Electron Microscopy of the explanted SIBS discs showed no signs of biodegradation.

Conclusion: SIBS material is intraorbitally and intraocularly biocompatible and does not encapsulate in the eye, and thus is suitable for use in aqueous drainage devices.

There have been described and illustrated herein several embodiments of glaucoma implant devices that divert aqueous humor from the anterior chamber of the eye and surgical methods associated therewith. While particular embodiments of the invention have been described, it is not intended that the invention be limited thereto, as it is intended that the invention be as broad in scope as the art will allow and that the specification be read likewise.

Thus, while particular methods of manufacture have been disclosed, it will be understood that other manufacture methods can be used. For example, because the copolymer materials described herein have a thermoplastic character, a variety of standard thermoplastic processing techniques can be used to for the devices described herein. Such techniques include compression molding, injection molding, blow molding, spinning, vacuum forming and calendaring, and extrusion into tubes and the like. Such devices can also be made using solvent-based techniques involving solvent casting, spin coating, solvent spraying, dipping, fiber forming, ink jet techniques and the like.

Also, while it is preferred that the implant device be realized by a simple tubular structure, it will be recognized that adaptations may be made of such structures. For example, other duct forming structures and shapes can be used. In another example, the device may include holes through the side wall of the tubular structure. In another example, the tubular structure may include multiple lumens therein.

It will therefore be appreciated by those skilled in the art that yet other modifications could be made to the provided invention without deviating from its spirit and scope as claimed.

What is claimed is:

1. An aqueous humor drainage device comprising:
   an elongate duct structure formed from a material, said material comprising polyisobutylene and a glassy segment, wherein said elongate duct structure provides a fluid passageway having a diameter less than 0.3 mm for diverting aqueous humor from the anterior chamber of the eye, and wherein said material resists obstruction of the elongate duct structure by cell encapsulation.

2. An aqueous humor drainage device according to claim 1, wherein:
   said elongate duct structure has a hardness with a range between Shore 10A and Shore 100D.

3. An aqueous humor drainage device according to claim 1, wherein:
   said glassy segment preferably does not contain any cleavable group which will release in the presence of body fluid inside the human eye and cause toxic side effects and cell encapsulation.

4. An aqueous humor drainage device according to claim 1, wherein:
   said glassy segment comprises a vinyl aromatic polymer.

5. An aqueous humor drainage device according to claim 4, wherein:
   said vinyl aromatic polymer comprises at least one of styrene and α-methylstyrene.

6. An aqueous humor drainage device according to claim 1, wherein:
   said glassy segment comprises a methacrylate polymer.

7. An aqueous humor drainage device according to claim 6, wherein:
   said methactylate polymer comprises at least one of methylmethacrylate, ethylmethacrylate, and hydroxymethalcrylate.

8. An aqueous humor drainage device according to claim 1, wherein:
   said material has a general block structure with a central elastomeric polyolefinic block and thermoplastic end blocks.

9. An aqueous humor drainage device according to claim 8, wherein:
   said material comprises a triblock polymer backbone comprising polystyrene-polyisobutylene-polystyrene.

10. An aqueous humor drainage device according to claim 8, wherein:
    said material has a general block structure selected from one of the following:
    a) BAB or ABA,
    b) B(AB)n or a(BA)n, and
    c) X-(AB)n or X-(BA)n;
    where A is an elastomeric polyolefinic block, B is a thermoplastic block, n is a positive whole number and X is a starting seed molecule.

11. An aqueous drainage device according to claim 10, wherein:
    wherein said material comprises one of a star-shaped block copolymer (where n=3 or more) and multi-dendrite-shaped block copolymer.

12. An aqueous humor drainage device according to claim 1, wherein:
    said fluid passageway has a diameter between 0.05 mm and 0.3 mm.

13. An aqueous humor drainage device according to claim 12, wherein: said fluid passageway has a diameter between 0.05 mm and 0.10 mm.

14. An aqueous humor drainage device according to claim 13, wherein:
    the elongate duct structure has an outside diameter less than 0.50 mm.

15. An aqueous humor drainage device according to claim 1, further comprising:
    a disk-shaped element and a retention member that are integral to said elongate duct structure and that are spaced apart such that the sclera of the eye is held therebetween in a manner that fixates said elongate duct structure.

16. An aqueous humor drainage device according to claim 15, wherein:
    said disk-shaped element and said retention member are angled with respect to a longitudinal axis of said elongate duct structure.

17. An aqueous humor drainage device according to claim 1, further comprising:
    retention means, disposed on the outer surface of said elongate duct structure, for fixating said elongate duct structure to the sclera of the eye.

18. An aqueous humor drainage device according to claim 17, wherein:
    said retention means comprises at least one of the following:
    a) at least one suture thread wrapped around said elongate duct structure;
    b) a silicon sleeve or other material that promotes scarring;
    c) a glue such as silastic adhesive; and
    d) at least one mechanical feature that is adapted to butt up against the sclera of the eye in order to limit at least one of posterior movement and anterior movement of said elongate duct structure.

19. An aqueous humor drainage device according to claim 1, wherein:
    said elongate duct structure is treated with an agent that prevents the fluid passageway from sticking closed in the event that it is pinched.

20. An aqueous humor drainage device according to claim 19, wherein:
    said agent is selected from the group consisting of hyaluronic acid, phosphatidyl choline, and glycerin.

* * * * *